United States Patent [19]
Bares

[11] Patent Number: 5,065,620
[45] Date of Patent: * Nov. 19, 1991

[54] METHOD AND APPARATUS FOR MEASURING THE PRINT QUALITY OF PRINT MEDIA RECEIVING INK JET INKS

[75] Inventor: Steven J. Bares, Corvallis, Oreg.

[73] Assignee: Hewlett-Packard Company, Palo Alto, Calif.

[*] Notice: The portion of the term of this patent subsequent to Mar. 27, 2007 has been disclaimed.

[21] Appl. No.: 610,615

[22] Filed: Nov. 8, 1990

Related U.S. Application Data

[60] Continuation-in-part of Ser. No. 358,100, May 30, 1989, abandoned, which is a division of Ser. No. 185,206, Apr. 22, 1988, Pat. No. 4,911,003.

[51] Int. Cl.$^5$ ............................................. G01N 13/00
[52] U.S. Cl. ............................................ 73/159; 73/73; 427/8; 118/713
[58] Field of Search ................. 73/73, 74, 75, 159, 73/150 R; 427/8; 118/713

[56] References Cited

U.S. PATENT DOCUMENTS

| 3,172,779 | 3/1965 | Warshaw et al. | 73/150 R |
|---|---|---|---|
| 3,336,796 | 8/1967 | Reynolds | 73/150 R |

FOREIGN PATENT DOCUMENTS

| 222956 | 1/1958 | Australia | 427/8 |
|---|---|---|---|
| 491097 | 2/1976 | U.S.S.R. | 73/150 R |
| 654178 | 6/1951 | United Kingdom | 427/8 |
| 792663 | 4/1958 | United Kingdom | 427/8 |
| 811795 | 4/1959 | United Kingdom | 427/8 |
| 830836 | 3/1960 | United Kingdom | 427/8 |
| 1068848 | 5/1967 | United Kingdom | 427/8 |

OTHER PUBLICATIONS

Bristow, J. A., "Liquid Absorption Into Paper During Short Time Intervals", Svensk Papperstidning, 19 (Oct. 15, 1967).

Primary Examiner—William A. Cuchlinski, Jr.
Assistant Examiner—Diego F. F. Gutierrez

[57] ABSTRACT

A method and apparatus for rapidly determining the print quality of a porous material which includes contacting a porous surface with a source of ink, providing a known relative acceleration between said ink source and said porous surface, and thereby transferring a predetermined volume of ink from said ink source to a known area of said porous suface. Then, the amount of ink transferred into the porous surface area per unit of time is measured to thereby determine the time between initial ink contact and the initial ink penetration, referred to as wetting delay, and the penetration rate of ink into the porous surface.

2 Claims, 3 Drawing Sheets

METHOD AND APPARATUS FOR MEASURING THE PRINT QUALITY OF PRINT MEDIA RECEIVING INK JET INKS

CROSS-REFERENCE TO RELATED APPLICATIONS

This application is a continuation-in-part of application Ser. No. 07/358,100 filed May 30, 1989, now abandoned, which in turn is a divisional application of Ser. No. 07/185,206 filed Apr. 22, 1988 and now issued as U.S. Pat. No. 4,911,003 on Mar. 27, 1990.

TECHNICAL FIELD

This invention relates generally to methods and apparatus for measuring the print quality of selected printed media and more particularly to the rapid measurement of the print quality of such media where ink jet inks have been ejected onto either plain or special paper.

BACKGROUND ART

In the field of testing and measuring the print quality of certain inks deposited on selected print media, it is known that the media print quality is related to the fluid (ink) penetration rate therein. The wetting delay of the fluid, or the time between initial fluid contact and initial fluid penetration, and the fluid penetration rate into the print media have been shown to closely correlate with ink jet print quality. That is, rapid fluid penetration rates and short wetting delays are indicative or a poor ink jet print quality or porous media injected with aqueous based inks.

One prior approach to measuring the print quality of aqueous based as well as other kinds of inks was developed by J. A. Bristow in 1967 and is described in an article by J. A. Bristow entitled "Liquid Absorption Into Paper During Short Time Intervals", *Svensk Papperstidning*, 19, Oct. 15, 1967. In the above Bristow process, a special type of ink jet head box is initially filled with a metered amount of the fluid under study. This head box is then placed in contact with the porous ink-receiving surface under study, and this surface is attached to a rotating wheel. By measuring the length of an ink trace for a number of different wheel speeds, a plot of the amount of fluid transferred into the porous material versus the time that the ink jet head box is in contact with the porous material can be developed for each of the wheel speeds. From this information, three parameters relating to the fluid penetration dynamics may be obtained, namely: (1) the volumetric roughness of the print medium, (2) the wetting delay of fluid penetration into the print medium and (3) the fluid penetration rate into the print medium.

Whereas the above described Bristow test has proven satisfactory in some respects, this process may take up to two to three hours to complete, and the test results obtained using the above Bristow method have been less than reliable in all circumstances. In addition, the equipment required by the Bristow method is sometimes awkward to set up and operate when collecting data during a plurality of head box runs in order to develop a plot having the multiple parameters described above.

DISCLOSURE OF INVENTION

The general purpose of this invention is to provide a new and improved method and apparatus for measuring certain parameters which correlate to the print quality of selected print media injected with certain inks. This method is capable of completion in a time on order of two to three minutes rather than two to three hours as in the above Bristow test. In addition, the reliability of test results thus produced in accordance with the present invention is improved relative to the Bristow test. And, the print quality measurement described and claimed herein may be carried out in a user-friendly and easy to operate environment in comparison to any known prior art.

To accomplish the above purpose and provide the above described advantages, I have discovered and developed a new and improved method and apparatus for measuring the print quality of selected print media on which certain inks have been deposited. This new approach includes the steps of initially contacting a porous surface with a source of ink and then providing a controlled relative acceleration between the ink source and the porous surface for thereby transferring a predetermined volume of ink from the ink source to a known area of the porous surface. The amount of ink transferred into the porous surface per unit time is measured in order to determine: (1) the time between initial contact and the initial ink penetration into the porous surface (the wetting delay), (2) the penetration rate of ink into the porous surface, and (3) the volumetric roughness of the porous surface.

In a first embodiment of the invention, a rotating wheel is used and is brought into contact with an ink source, whereafter a predetermined acceleration is provided between a porous surface on the periphery of the wheel and the ink source in contact therewith.

In a second embodiment of the invention, a porous material is provided on a rotating platen, and an ink source is brought into contact with the porous material which is rotating at a constant velocity. Then, the ink source may be accelerated inwardly of the rotating platen on one of the radii thereof or decelerated outwardly of the rotating platen on one of the radii thereof to provide the necessary relative acceleration between the ink source and the porous material under test. In this manner, the amount of ink transferred into the porous surface area per unit time may be rapidly measured to determine the wetting delay, the ink penetration rate into the porous surface and the volumetric roughness thereof.

The various advantages and novel features of this invention will become better understood with reference to the following description of the accompanying drawings.

DETAILED DESCRIPTION OF THE INVENTION

Figure 1A:
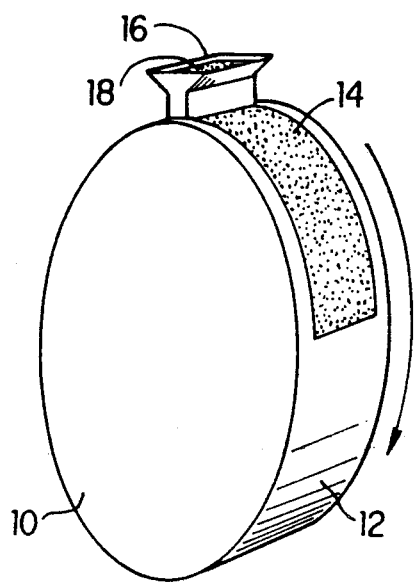
FIGS. 1A and 1B are abbreviated isometric view illustrating the constant rotational velocity print quality measuring technique of the prior art.
Figure 1B:
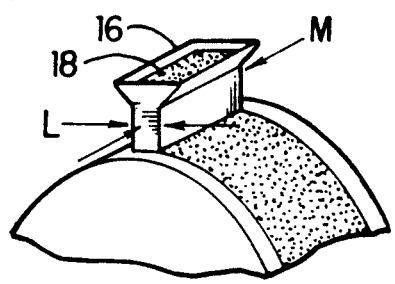
Figure 1C:
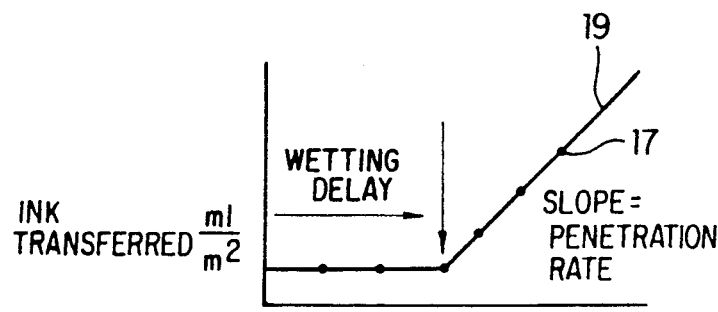
FIG. 1C is a plot of ink transferred in FIG. 1A versus ink source contact time on the porous material for a number of ink traces. This plot is obtained by connecting a plurality of data points provided by the number of individual runs used to obtain the plurality of ink traces on a number of different paper samples mounted on the periphery of the wheel.

Referring now to FIGS. 1A and 1B, this assembly includes a cylindrical wheel 10 having a smooth outer surface 12 thereon for receiving strips 14 of a porous medium, such as plain paper, which are situated to undergo a series of ink tracing steps. In each of these steps, an ink head box 16 filled with a chosen ink 18, is brought in contact with the paper 14 which is rotated at a constant velocity. The contact time that the ink head box 16 is in contact with the paper 14 is equal to L/V, where L is the length of the lower end of the head box 16 and V is the constant tangential velocity of the wheel 10. The head box 16 has an aperture length, L, and a width dimension M as shown in FIG. 1B. The length of the ink trace left on the paper 14, of width M, is measured, and the time required for the fluid absorption is then calculated from knowing the wheel tangential velocity. By measuring the length of ink traces at a variety of different wheel speeds, a plot of the amount of fluid transferred versus contact time may be constructed. Such a plot is shown in FIG. 1C, and three parameters that relate to the fluid penetration dynamics are obtained from this plot. These parameters are the volumetric roughness of the print medium, the wetting delay, and the fluid penetration rate. As indicated above, the wetting delay and the penetration rate have been shown to correlate with ink jet print quality.

Using the above described Bristow method, it takes one individual test run as described to obtain just one of the data points 17 on the plot in FIG. 1C, with the overall test time required to obtain the entire plot 19 being between one and three hours. As indicated in FIG. 1C, the wetting delay is equal to the time at which the plot 19 turns upwardly into the upper right hand quadrant, and the slope of the plot 19 is equal to the fluid penetration rate. The plot intercept of the vertical axis in FIG. 1C is equal to the volumetric roughness of the porous surface under test.

As previously noted, one significant disadvantage of the Bristow test is the long time it takes to complete the plot 19 of FIG. 1C and thereby determine the print quality of a given print media. This long test time requirement has prevented the Bristow test from being incorporated into paper mill production situations, for example.

Figure 2A:
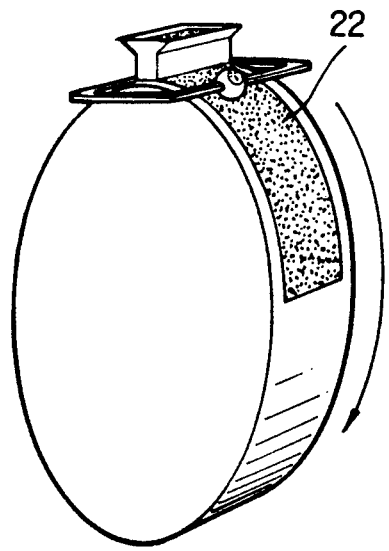
FIGS. 2A and 2B are abbreviated isometric views illustrating the wheel acceleration and corresponding ink source depletion rate test in accordance with the present invention.
Figure 2B:
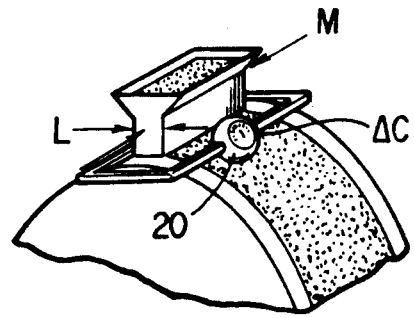

In order to overcome the long time problem associated with the prior art Bristow test and in accordance with the present invention, it is proposed to accelerate the wheel as indicated in FIGS. 2A and 2B and to use an ink depletion rate measuring device 20 connected to the head box 16. This measuring device 20 may, for example, be a device for measuring a change in either conductance or capacitance, $\Delta C$ in the head box 16 associated with forming a given ink trace 22 as the wheel 10 is accelerated over a given distance beginning at time $t=0$.

The amount of fluid transferred per unit area, $dV_t/dA$, is given in differential form by the expression:

$$dV_t/dA = (1/M) \cdot (dV_t/dt) \cdot (dt/dx), \tag{1}$$

where x is equal to the length of an ink trace. If the wheel in FIGS. 2A and 2B begins accelerating at $t=0$ and the headbox makes contact at $t=t'$, then this expression becomes:

$$dV_t/dA = (1/M) \cdot (dV_t/dt) \cdot (1/at), \tag{2}$$

where a is equal to wheel acceleration relative to the headbox. Under these conditions the ink headbox contact time is given as a function of the instantaneous velocity, $V(t)$, by the expression:

$$contact\ time = L/V(t) = L/at. \tag{3}$$

Experimentally, $dV_t/dA$ would be plotted versus the square root of the contact time. If the standard wheel approach in FIG. 2 were used, then the acceleration, a, will be the wheel acceleration.

A numerical analysis of this rotating wheel embodiment of the invention is given below using the following typical values for acceleration rate and ink headbox geometry.

Acceleration rate = 0.04 cm/sec$^2$

Ink headbox geometry  $M = 1$ cm
$L = 0.1$ cm

Figure 3A:
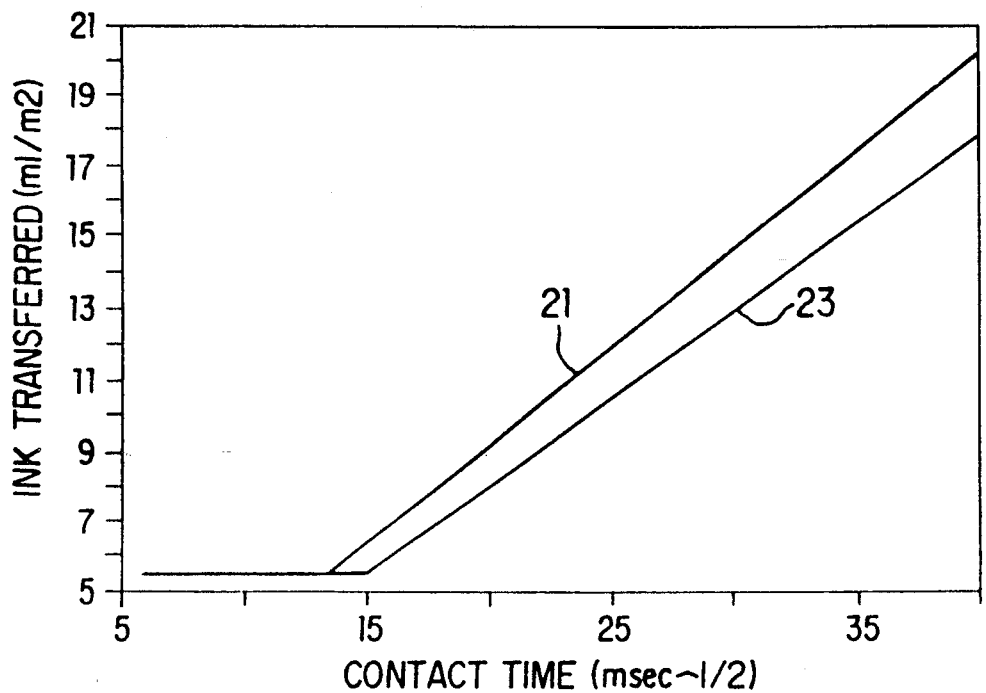
FIG. 3A is a computer simulation plot of the ink transferred per unit area into the porous medium under test as a function of ink contact time using the measuring apparatus and method illustrated in FIGS. 2A and 2B.
Figure 3B:
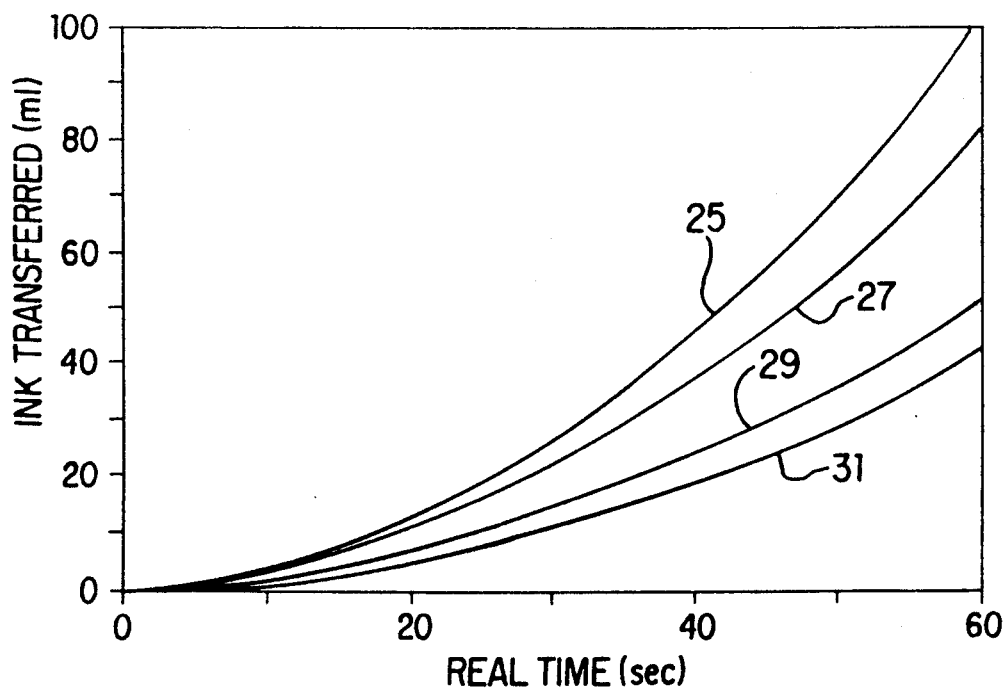
FIG. 3B is a computer simulation plot of ink transferred into the porous medium per unit of real time using the method and apparatus illustrated in FIGS. 2A and 2B.

Xerographic paper parameters with typical ink jet ink:

wetting delay = 14(msec)$^{\frac{1}{2}}$ volumetric roughness = 5.5 ml/m$^2$ penetration rate = 0.6 ml/m$^2$(msec)$^{\frac{1}{2}}$ Using this numerical data together with equations (1) and (2) above, plots of the volume of ink transferred are obtained by computer simulation and are shown in FIGS. 3A and 3B. To perform the simulation, two sets of parameters describing the ink/paper combination were assumed as input. One set was used to generate curve 21 in FIG. 3A, and this set assumed a wetting delay, $W_D = 14$ ms$^{\frac{1}{2}}$, a volumetric roughness, $V_R = 5.5$ ml/m$^2$, and a penetration rate, $P_R$ equal to 0.6 ml/m$^2$ms$^{\frac{1}{2}}$. Another set of parameters was assumed in order to generate curve 23 in FIG. 3A, and this set assumed a wetting delay, $W_D$, equal to 15 ms$^{\frac{1}{2}}$, a volumetric roughness, $V_R$, equal to 5.5 ml/m$^2$, and a penetration rate, $P_R$, equal to 0.5 ml/m$^2$ms$^{\frac{1}{2}}$. Both of these sets of parameters are readily obtainable using the standard Bristow apparatus.

The total time for this simulated experiment was approximately 60 seconds, yet the entire Bristow curve was obtained. Also note that it was not necessary to measure an accurate quantity of fluid in the headbox since the experiment only needs to measure $dV_t/dt$.

This feature further reduces the time it takes to complete a measurement. Furthermore, using this technique the required headbox velocity as a function of time can be preprogrammed into an instrument, or it can be measured via an optically encoded wheel or platen, thus simplifying the mechanical system.

An instrument which performs this measurement can be equipped with not only the necessary data acquisition equipment, but also the necessary software to analyze the Bristow curve and return the above three parameters of interest to ink jet print quality. Also, by adjusting the magnitude of the wheel's acceleration rate, the instrument can be used for measuring the parameters of interest in either non-absorbent papers or for very absorbent special ink jet papers.

The test and measurement method according to the present invention depends on the ability to accurately measure the quantity, $dVt/dt$. The simulation techniques used herein shows that for non-absorbent plain papers, the change in headbox ink volume ranges from zero to 100 microliters per second. Absorbent specialty ink jet papers can have ten times the above penetration rate, and hence can have volume changes of zero to 1000 microliters change in ink volume per second.

Several methods for measuring $dVt/dt$ at the headbox are available. One method is to make the ink headbox out of two halves of aluminum, separated by a non-conductive film. Depending upon the conductivity of the fluid, the capacitance or conductance of the headbox assembly will change as the ink flows from the headbox. This parameter can be calibrated to yield accurate changes in ink volume. Alternatively, the headbox can be lined with a carbon layer or other high resistance, inert material. As the ink flows out of the headbox, the level of fluid will decrease and cause the resistance from top to bottom to change. A third option would be to use a laser/photodiode arrangement to detect the change in the level of the fluid in the headbox. This approach would also be calibrated to yield headbox ink volume information.

The above described embodiment of the present invention possesses at least three distinct advantages over conventional prior art Bristow test procedures. First of all, the above described embodiment will yield the entire Bristow curve in related ink jet parameters in less than two minutes, as compared two or more hours to complete the standard Bristow test. Thus, the present invention as described above will be ideal for use in a conventional paper mill production operation.

Secondly, data acquisition using this technique can be designed to take many data points in the regions of interest of the Bristow curve. That is, more data can be taken in the low velocity regions of headbox travel to obtain more reliable ink penetration rates at slower speeds. The larger number of data points obtained will improve the least-square fit to the data to yield the ink penetration rate. This improved reliability will not be at the expense of vast amounts of time, and any additional time required to complete the test will be negligible. Furthermore, this technique places a lower limit on the error of the measurement as compared to the error caused by paper and ink variations from sample to sample.

Thirdly, the user must only install the paper sample and check to see that the headbox has sufficient ink therein in order to complete the measurement (no pipettes required). The paper sample is mounted and a start button is pressed. After two minutes the complete Bristow curve is returned with the above described ink jet parameters calculated.

Referring again to FIG. 3A, the volumetric roughness of both plots 21 and 23 was assumed to be 5.5 ml/m$^2$, and the penetration rates for these two curves 21 and 23 were assumed to be 0.6 and 0.5 ml/m$^2$·msec$^{\frac{1}{2}}$, respectively. The wetting delays for these two curves 21 and 23 were assumed to be 14 and 15 msec$^{\frac{1}{2}}$, respectively.

In FIG. 3B, the plot or curve 25 represents calculated values of $dVt/dt$ in units of microliters per second for curve 21 in FIG. 3A. The plot 27 represents calculated values of $dVt/dt$ in units of microliters per second for curve 23 in FIG. 3A, and curve 29 represents calculated values for the total fluid transferred in milliliters for curve 21 in FIG. 3A. Finally, curve 31 represents the calculated values of the total fluid transferred for curve 23 in FIG. 3A. The total time for the above experiment was 60 seconds. The simulations performed show that the entire curve needed to evaluate the three parameters of interest herein can be measured in a one minute experiment.

This numerical simulation also shows that with typical values describing a paper/ink combination (curves 21 and 23 in FIG. 3A), we can easily measure the flux, $dVt/dt$, of ink exiting the headbox of the apparatus shown in the drawings. In evaluating the total volume exiting the ink headbox after the experiment to determine Vt, a small total volume of ink is used. This translates into a convenient instrument, since few refills of the headbox are required after multiple runs.

In this numerical simulation, we assume typical values for the headbox geometry, wheel acceleration rates, and the two sets of parameters noted for curves 21 and 23 in FIG. 3A. Then, curves 27 and 31 in FIG. 3B were generated and are the calculated values of $dV/dt$ and Vt with the assumed parameters from curve 23. The curves 25 and 29 are the calculated values of $dVt/dt$ and Vt with the assumed parameters from curve 21 in FIG. 3A. During operation, the flux of ink exiting the headbox, or $dVt/dt$, will be measured. Then, with the knowledge of the acceleration rate as a function of time and with knowledge of the ink flux, $dVt/dt$, a plot of the volume of ink transferred versus contact time can be constructed using equations 2 and 3. Also, the larger number of data points obtained will improve the reliability of the penetration rate, wetting delay and volumetric roughness data extracted from a particular run.

Figure 4A:
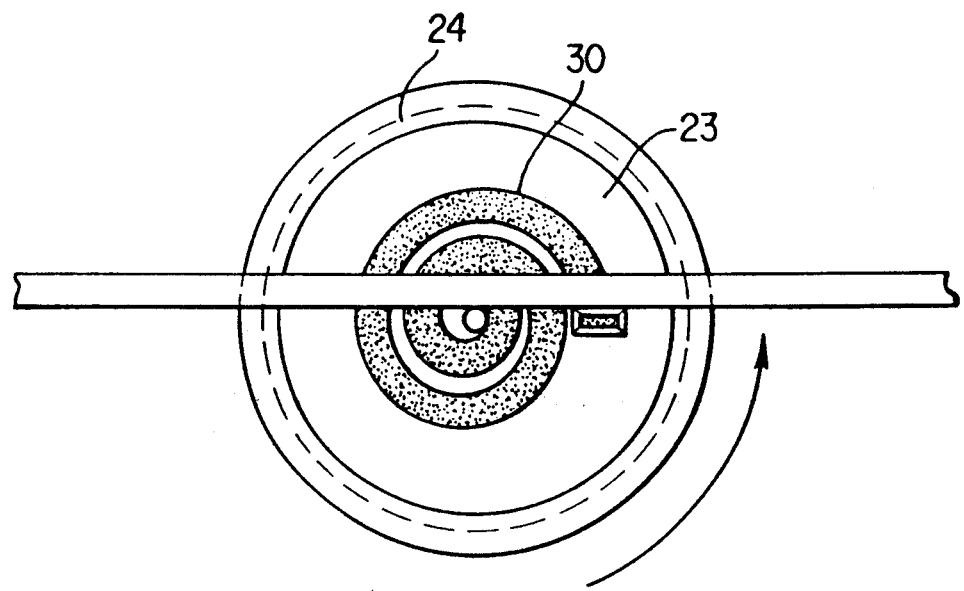
FIGS. 4A and 4B are plan and elevation views, respectively, illustrating the second embodiment of this invention employing the platter-type rotational platen for receiving the porous material under test. This material makes contact with an ink head box which may be either accelerated or decelerated with respect to the porous medium as it moves inwardly or outwardly, respectively, on a selected radius of the rotating platen.
Figure 4B:
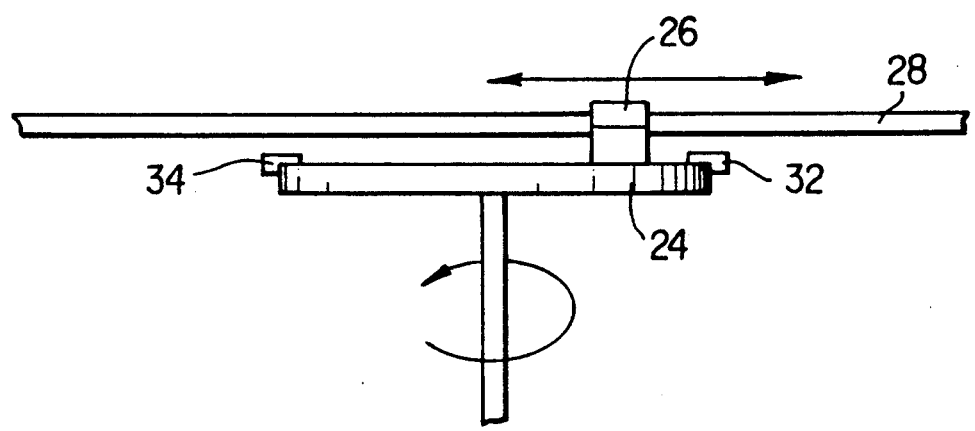

Referring now to FIGS. 4A and 4B, there is shown in plan and cross-section views, respectively, a second embodiment of the present invention wherein the print medium 23 under test is mounted on the top cylindrical surface of the circular platen 24. An ink supply headbox 26 is mounted on a horizontal slide bar 28 and is operative to move either inwardly or outwardly on the slide bar 28 at a constant velocity. The platen 24 is decelerated if the headbox 26 makes contact with the platen and moves outwardly, and is accelerated if the headbox 26 moves inwardly toward the center of the platen from the outside.

The headbox movement in FIGS. 4A and 4B occurs over the surfaces of the porous medium 23 in all directions and not just in one direction as in the rotating wheel test of the earlier described embodiment. Since fiber orientation is not isotropic in a typical paper, this technique yields an output that measures ink penetration rates independent of the paper formation. Furthermore, since ink drop penetration occurs in all directions over the paper surface, integrating the penetration rates over the fiber direction will improve the test correlation to the ink jet print quality.

Using the circular, spiral trace motion as indicated by the spiral swath 30 in FIG. 4A, it is possible to obtain much longer traces than those obtainable using the above rotating wheel approach. This feature improves the reliability of the attained results. For example, for the test described here using an 8½" diameter platen, a trace length of 280 centimeters is available. Therefore, larger ink volumes, longer traces and hence better results may be obtained.

Finally, the speed of the test illustrated in FIGS. 4A and 4B is enhanced by the simple clamping arrangement shown wherein a pair of peripheral magnetic clamps 32 and 34 may be easily secured to the outer edges of the rotating platen 24 to temporarily secure the printed samples 23 in place for the duration of the printing test.

Various modifications may be made in the above described embodiments without departing from the scope of this invention. For example, many changes in shape, form, design and geometry of the illustrated apparatus are within the skill of the art and may well be appropriate for a particular print quality measuring application. Accordingly, the present invention is limited only by the reasonable scope of the following appended claims.

I claim:

1. A method for evaluating the print quality of a porous material which includes the steps of:
   a. contacting a porous surface of said porous material with a source of ink,
   b. providing a known relative acceleration between said ink source and said porous surface, thereby
   c. transferring a measurable volume of ink from said ink source to a known area of said porous surface, and
   d. measuring the amount of ink transferred into said porous surface per unit of time, whereby the ink wetting delay and ink penetration rate into said porous surface which correlate with the ink jet print quality may be determined.

2. Apparatus for evaluating the print quality of a porous material including, in combination:
   a. means for contacting a porous surface of said porous material with a source of ink,
   b. means associated with said source of ink for providing a known relative acceleration between said ink source and said porous surface,
   c. means adjacent to said porous surface for transferring a measurable volume of ink from said ink source to a known area of said porous surface, and
   d. means connected to said source of ink for measuring the amount of ink transferred into said porous surface area per unit of time, whereby the ink wetting delay and ink penetration rate into said porous surface which correlate with the ink jet print quality may be determined.

* * * * *